(12) United States Patent
Ivanko et al.

(10) Patent No.: US 6,558,407 B1
(45) Date of Patent: *May 6, 2003

(54) BREAST STABILIZER WITH INSTRUMENT GUIDE

(75) Inventors: David Ivanko, Bridgeport, CT (US); Frank J. Viola, Sandy Hook, CT (US)

(73) Assignee: Tyco Healthcare Group LP, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/694,854

(22) Filed: Oct. 24, 2000

(51) Int. Cl.$^7$ ............................................. A61B 17/00
(52) U.S. Cl. ....................................... 606/201; 606/130
(58) Field of Search .................................. 606/201, 130, 606/202, 203; 600/235, 562, 565, 407, 410, 421

(56) References Cited

U.S. PATENT DOCUMENTS

| | | | |
|---|---|---|---|
| 5,308,321 A | * | 5/1994 | Castro ........................ 606/201 |
| 5,947,896 A | | 9/1999 | Sherts et al. |
| 5,976,080 A | | 11/1999 | Farascioni |
| D420,130 S | | 2/2000 | Nicholas et al. |
| 6,102,853 A | | 8/2000 | Scirica et al. |
| 6,213,940 B1 | | 4/2001 | Sherts et al. |
| 6,254,614 B1 | * | 7/2001 | Jesseph ....................... 606/130 |

OTHER PUBLICATIONS

"Mini–CABG Beating Heart Instrumentation"; Vascular Therapies; 1998.

* cited by examiner

Primary Examiner—Kevin T. Truong

(57) ABSTRACT

A breast stabilizing and support device has a generally oval base with a central opening therethrough, a variable diameter cord or band positioned concentrically within the central opening and adapted to be slid over the breast and tightened at the breast base to cause the breast to bulge firmly away from the base, and one or more articulated arms that are adapted to be attached to and adjustably positioned around the base for holding various instruments. The base is semi-rigid and compliant to form around the contours of the torso adjacent to the breast. Attached to the base and lying in the central opening is a loop of cord that is adjustable in diameter and adapted to surround and apply a radially inward, compressive force to the breast. One or more articulated arms have selectively lockable clamps at one end for securing the arms to the base at various positions. At another end the arms have attachment means such as jaws or clamps for securing one or more tools to the base and in position to perform operations on the breast tissue.

15 Claims, 2 Drawing Sheets

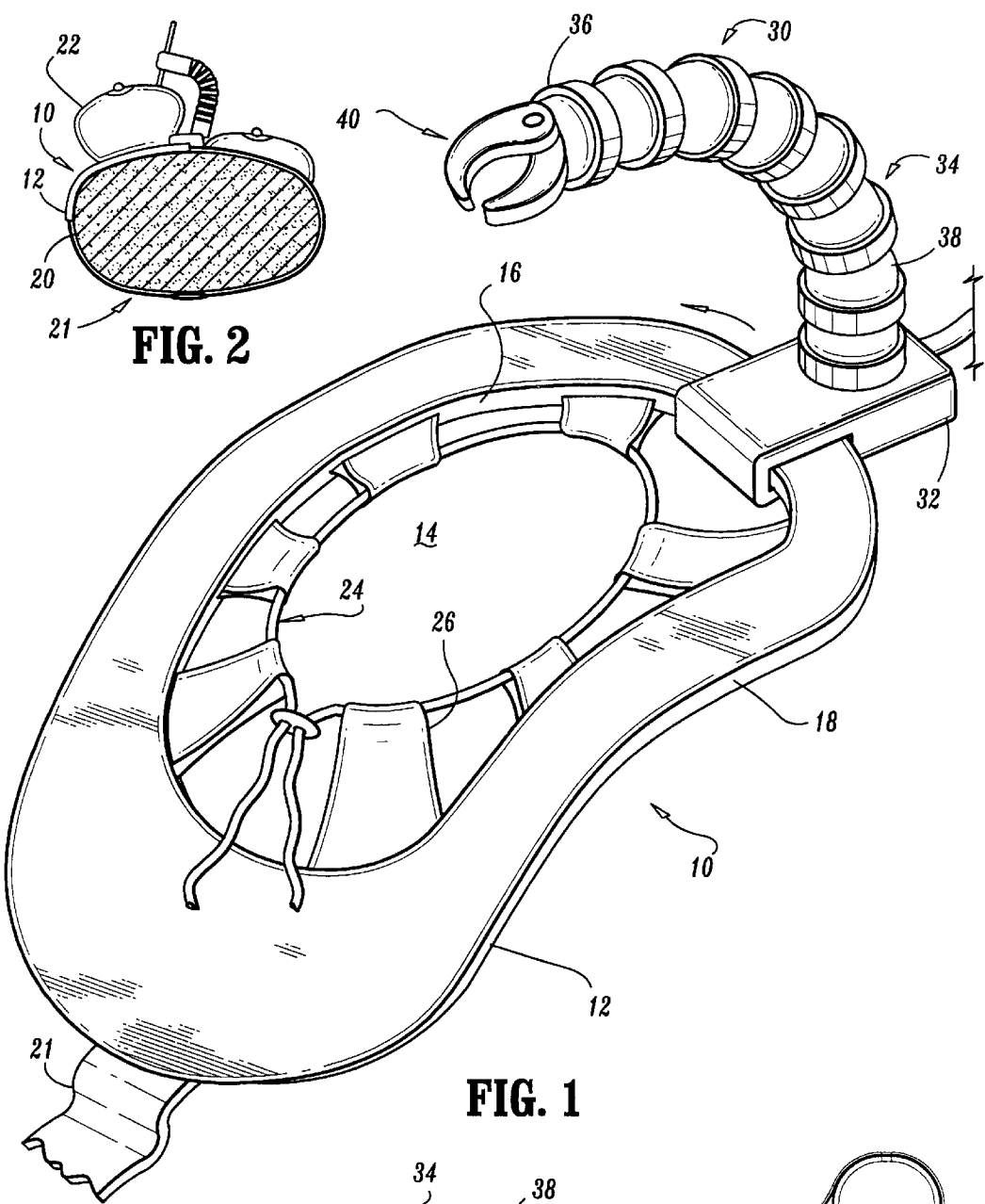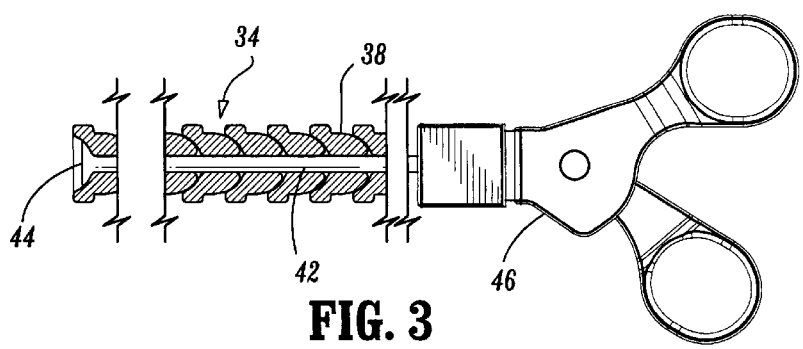

BREAST STABILIZER WITH INSTRUMENT GUIDE

TECHNICAL FIELD

The present invention relates to a breast-stabilizing device and, more particularly, to a breast stabilizing device used to position the breast during medical procedures, and having instrument guide accessories.

BACKGROUND OF THE INVENTION

During various medical procedures involving the breast, such as biopsy sample removal or other surgical procedures, it is desirable to stabilize and securely hold in position the breast tissue. Stabilizing and holding the tissue facilitates precise locating techniques for specific areas or features within the tissue. This is particularly critical in instances where, for example, ultrasound or other imaging techniques are employed and relied upon for removal of tissue or placement of objects and instruments. By securely locating and stabilizing the tissue in the breast, such procedures as fine needle aspiration biopsy, core needle biopsy, and vacuum-assisted biopsy can be carried out more accurately and expediently.

In certain surgical or other medical procedures, including those performed on the breast, it is desirable to provide a support base for attaching instrument guides or instruments, such as retractors. Support bases that surround an operational area on the body and facilitate holding or stabilizing of instruments exist for some types of procedures, such as the Mini-CABG™ articulated arm manufactured and sold by United States Surgical Corporation.

SUMMARY OF THE PRESENT INVENTION

It is an object of the present invention to provide a device for supporting the breast in a stabilized position such that the internal tissue of the breast is stabilized during various procedures. It is a further object to provide such a device that also facilitates the placement and holding of instruments. These objects and others are achieved by the present invention.

The present invention is directed to a breast stabilizing and support device having a generally oval base with a central opening therethrough, a variable diameter cord or band positioned concentrically within the central opening and adapted to be slid over the breast and tightened at the breast base to cause the breast to bulge firmly away from the base, and one or more articulated arms that are adapted to be attached to and adjustably positioned around the base for holding various instruments. In the preferred embodiment, the base is semi-rigid and compliant to form around the contours of the torso adjacent to the breast. Attached to the base and lying in the central opening is a loop of cord that is adjustable in diameter and adapted to surround and apply a radially inward, compressive force to the breast. One or more articulated arms have selectively lockable clamps at one end for securing the arms to the base at various positions. At another end the arms have attachment means such as jaws or clamps for securing one or more tools to the base and in position to perform operations on the breast tissue.

BRIEF DESCRIPTION OF THE DRAWINGS

FIG. 1 is a schematic, perspective view of a breast-stabilizing device according to a first embodiment of the present invention.

FIG. 2 is a schematic front view of the present invention device of FIG. 1 shown attached to a human body (in cross-section).

FIG. 3 is a schematic, partial side view of an articulated arm body of the present invention device.

DESCRIPTION OF THE PREFERRED EMBODIMENTS

Figure 4:
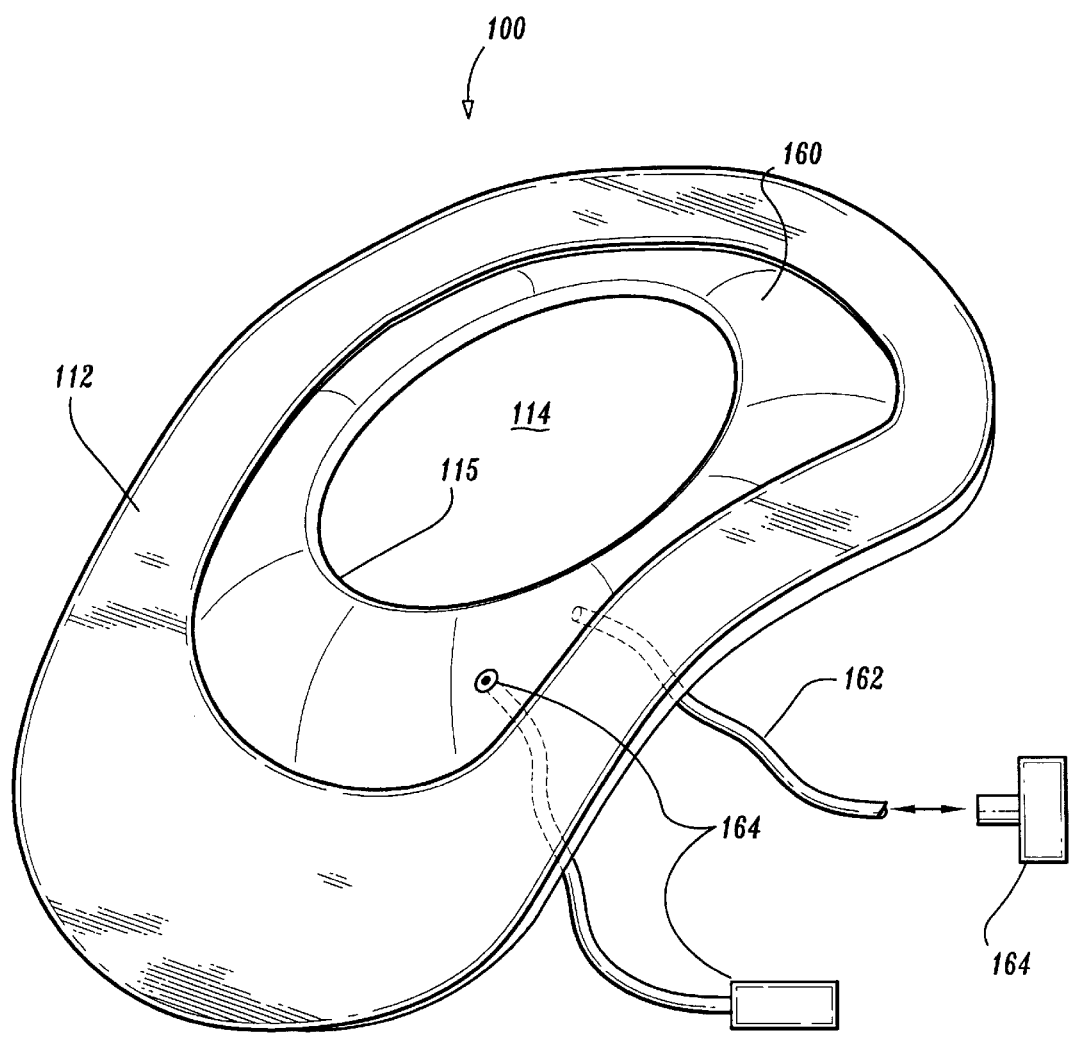
FIG. 4 is a schematic, perspective view of a breast-stabilizing device according to a second embodiment of the present inventions.

Referring to FIGS. 1–2, a breast stabilizing device (10) according to the present invention includes a base (12) having a central opening (14) therethrough. The base (12) has inner (16) and outer (18) sidewalls. The base (12) is preferably made from a semi-rigid material that is sufficiently compliant to form around the contours of the body at the torso (20) when the central opening (14) is slid over a breast (22). Alternatively, the base (12) may be made from a rigid material having a predetermined curvature designed to generally coincide with typical torso curvature. The base (12) may also be made from a series of linked, relatively pivotable segments or it may be made from a rigid material having thin radial grooves to form compliant rib sections. A non-rigid material may also be employed for maximum compliance. The underside of the base (12), regardless of the material selected for the base (12), is preferably coated with a layer of soft, frictional material such as rubber to resist sliding or movement relative to the body (20).

An adjustable-diameter loop (24) positioned concentrically within the central opening (14) of the base (12) is attached to the base (12) by elastic cord members or elastic loops (26) as shown. The adjustable loop (24) may be a cord having a slideable buckle (28) as shown, or other diameter-adjusting means. It may be made of elastic or inelastic material. Alternatively, the adjustable loop (24) may be a non-adjustable, elastic loop sized to be stretched, thereby imparting radially inward, compressive force on a breast.

The breast stabilizing device (10) is positioned on a breast (22) by adjusting or stretching the loop (24) to fit around the breast (22). It is then slid over the breast (22) and the loop (24) is positioned at or near the base of the breast (22) adjacent to the torso (20). A strap (21) is used to wrap around the torso (22) to secure the device (10) to the body. The loop (24) is then tightened by adjusting the buckle (28) or, if applicable, releasing an elastic loop (24) from a stretched state to impart a radially inward, compressive force around the base of the breast (22). The compressive force should be sufficient to cause the internal tissue of the breast (22) to be biased away from the torso (20) and to firmly fill out the skin of the breast, thereby stabilizing the internal tissue against incidental, relative movement.

One or more articulated arms such as the articulated arm (30) shown in FIGS. 1–2 are adapted to be selectively attached to and positioned about the base (12). Each arm (30) includes a clamp base (32) adapted to be clamped to and released from the base (32) by a conventional type clamp that engages the base (12) at, for example, the inner and outer side walls (16, 18). The arm body (34) is preferably flexible to enable selective positioning of a distal end (36) of the arm body (34) relative to the base (12). The arm body (34) may be comprised of, as shown in the preferred embodiment, a series of universal joints (38) for maximum variability. At the distal end (36), an instrument attaching mechanism, such as a jaw (40), clamp, or the like is provided for holding and positioning an instrument, retractor or other device. The arm body (34) may be compliant by including, for example, a deformable wire core.

In the preferred embodiment, the arm body (34) includes a tension wire core (42) with an anchor (44) at its distal end, running through the universal joints (38) and being attached to a lever mechanism (46) so that an operator may selectively loosen or tension the wire core (46) to adjust or lock, respectively, the relative position of the arm body (34), as shown in FIG. 3.

Alternatively, as shown in FIG. 4, a breast stabilizing device (100) similar to that described with respect to FIGS. 1–3, may include an inflatable ring (160) positioned concentrically inside the central opening (114) of the base (112) instead of the loop (24) of the embodiment of FIGS. 1–3. The inflatable ring (160) includes inflation means such as an inflation conduit (162) attached to a pressurized gas source (164) and at least one deflation valve (164). The breast stabilizing device (100) is fitted over a breast by sliding the central opening (114) over the breast while the ring (160) is in a deflated state. Once the base (112) is seated against the torso, and the inner diameter (115) of the ring (114) is positioned near the base of the breast, the ring (114) is inflated with sufficient volume and pressure to cause the internal tissue of the breast (22) to be biased away from the torso (20) and to firmly fill out the skin of the breast, thereby stabilizing the internal tissue against incidental, relative movement. To release the breast and remove the device (100), the ring (114) is deflated through the valve (164).

While the preferred embodiments of the present invention have been herein described, it is understood and acknowledged that variation and modification may be made thereto without departing from the scope of the presently claimed invention.

What is claimed is:

1. A breast stabilizing device comprising
    a base;
    a loop-shaped pressurizing member fixed to said base and adapted to surround a breast and apply radially inward, compressive force to said breast.
2. A device according to claim 1, wherein
    said base is generally flat and is adapted to engage the torso of a body at the base of said breast.
3. A device according to claim 1, wherein
    said base includes a central opening and is adapted to mount said pressurizing member therein, such that said central opening fits around said breast when said pressurizing member surrounds said breast.
4. A device according to claim 1, wherein
    said pressurizing member comprises an elastic loop.
5. A device according to claim 1, wherein
    said pressurizing member comprises a length-adjustable cord elastically attached to said base.
6. A device according to claim 1, wherein
    said pressurizing member comprises an inflatable ring.
7. A device according to claim 1, further comprising
    a strap attached to said base and adapted to secure said base to a body of a medical patient.
8. A device according to claim 1, further comprising
    at least one instrument arm attached at its proximal end to said base and having instrument attaching means at its distal end for securely attaching and positioning an instrument relative to said base.
9. A device according to claim 8, wherein
    said instrument arm proximal end is selectively positionable relative to said base.
10. A device according to claim 8, wherein
    said instrument arm distal end is selectively positionable relative to said base.
11. A device according to claim 8, wherein
    said instrument arm comprises a base having locking means at its proximal end for selectively locking said instrument to said base at variable positions relative to said base; and
    said instrument arm comprises instrument-attaching means at its distal end for selectively attaching an instrument to said instrument arm.
12. A device according to claim 8, wherein
    said instrument arm is deformable, thereby being adapted to position the distal end of said instrument arm relative to its proximal end.
13. A device according to claim 12, wherein
    said instrument arm comprises arm locking means for selectively locking and unlocking said instrument arm in various positions in which said distal end is positioned relative to said proximal end, successively.
14. A device according to claim 12, wherein
    said instrument arm comprises a series of articulate joints.
15. A breast stabilizing device comprising
    a base;
    a loop-shaped pressurizing member fixed to said base and adapted to surround a breast and apply radially inward, compressive force to said breast;
    at least one instrument arm attached at its proximal end to said base and having instrument attaching means at its distal end for securely attaching and positioning an instrument relative to said base, said instrument arm being deformable, thereby being adapted to position the distal end of said instrument arm relative to its proximal end;
    said instrument arm comprises a series of articulate joints; and
    said arm locking means comprise a tension cable threaded through said joints and anchored at one end of said instrument arm, and adapted to be selectively tensioned to cause said joints to lock relative to each other.

* * * * *